United States Patent
Kim (10) Patent No.: US 10,054,571 B2
(45) Date of Patent: Aug. 21, 2018

(54) MONOAZO-BASED DYE FOR ACID DETECTION

(71) Applicant: KYUNGPOOK NATIONAL UNIVERSITY INDUSTRY-ACADEMIC COOPERATION FOUNDATION, Daegu (KR)

(72) Inventor: Tae Kyeong Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 15/103,627

(22) PCT Filed: Oct. 17, 2014

(86) PCT No.: PCT/KR2014/009805
§ 371 (c)(1),
(2) Date: Jun. 10, 2016

(87) PCT Pub. No.: WO2015/088134
PCT Pub. Date: Jun. 18, 2015

(65) Prior Publication Data
US 2016/0327529 A1    Nov. 10, 2016

(30) Foreign Application Priority Data

Dec. 10, 2013    (KR) .................. 10-2013-0153460

(51) Int. Cl.
*G01N 33/00*    (2006.01)
*G01N 31/22*    (2006.01)
(Continued)

(52) U.S. Cl.
CPC ....... *G01N 31/224* (2013.01); *C09B 29/0003* (2013.01); *C09B 29/081* (2013.01); *D06P 1/004* (2013.01); *G01N 31/221* (2013.01)

(58) Field of Classification Search
None
See application file for complete search history.

(56) References Cited

U.S. PATENT DOCUMENTS 6,391,626 B1 * 5/2002 Adams .................. C12Q 1/04
435/287.9

FOREIGN PATENT DOCUMENTS

KR    10-0910170 B1    5/2009
KR    10-1172860 B1    9/2011
(Continued)

OTHER PUBLICATIONS

International Search Report dated Jan. 16, 2015, with English Translation, in Corresponding Application PCT/KR2014/009805 (4 pages).
(Continued)

*Primary Examiner* — Xiaoyun R Xu
(74) *Attorney, Agent, or Firm* — Hovey Williams LLP (57) ABSTRACT

The present invention relates to a monoazo-based dye for acid detection, which changes color upon addition of or exposure to acid and, more specifically, to a dye which changes color within a few seconds upon exposure to a trace amount of a strong acidic material, and a fiber product using the same. The monoazo-based dye for acid detection according to the present invention has an effect of reacting with a trace amount of strong acid to change color, and returning to the original color when the acid is removed. Also, a fiber dyed with the dye of the present invention exhibits high color fastness and thus is not discolored and faded by laundering or sunlight. In addition, there is an effect of
(Continued)

Yellow

Acid Adsorption ⇌ Acid Removal

Red preventing secondary contamination at an accident scene and serious accidents from harmful environmental factors, when protective or working clothes are manufactured applying the effect, thereby providing a function enabling workers to recognize an exposure to acid in real time in the case of an exposure to an acid-contaminated environment.

7 Claims, 4 Drawing Sheets (51) Int. Cl.
 C09B 29/01 (2006.01)
 D06P 1/00 (2006.01)
 C09B 29/08 (2006.01)

(56) References Cited

FOREIGN PATENT DOCUMENTS

KR 10-1230098 B1 11/2012
KR 10-1339336 B1 12/2013

OTHER PUBLICATIONS

Written Opinion of the International Searching Authority dated Jan. 16, 2015, with English Translation, in Corresponding Application PCT/KR2014/009805 (10 pages).
Kim, Taekyeong et al., Synthesis and Application of Alkyl-substituted High Chroma Yellow Dyes for Unmodified Polypropylene Fiber, Fibers and Polymers 2009, vol. 10, No. 2, pp. 148-153 (6 pages).
Jo, Nayeong et al., Synthesis Yield Improvement of Acid Gas Sensing Dye, 2013 Fall Conference of the Korean Fiber Society, Oct. 17-18, 2013, p. 283, with English Translation (4 pages).
Song, Hwan-Moon et al., Fabrication of Chemical Sensors for the Detection of Acidic Gas using 1,3-bisdicyanovinylindane, Korean Chem. Eng. Res., vol. 46, No. 1, Feb. 2008, pp. 184-188 (5 pages).
Smith, Graham Smith, Proton transfer versus nontransfer in compounds of the diazo-dye precursor 4-(phenyldiazenyl)aniline (aniline yellow) with strong organic acids: the 5-sulfosalicylate and the dichroic benzenesulfonate salts, and the 1:2 adduct with 3,5-dinitrobenzoic acid, Crystal Structure Communications, Acta Cryst. (2009). C65, o543-o548 (7 pages).

* cited by examiner

FIG. 1

Yellow           Red

MONOAZO-BASED DYE FOR ACID DETECTION

RELATED APPLICATIONS

This application is the National Stage of International Patent Application No. PCT/KR2014/009805, filed Oct. 17, 2014, which is hereby incorporated by reference in its entirety, and which claims priority to Korean Patent Application No. 10-2013-0153460, filed Dec. 10, 2013.

TECHNICAL FIELD

The present invention relates to a monoazo-based dye for acid detection, which changes color upon addition of or exposure to acid, and more specifically, to a dye which changes color within a few seconds upon exposure to a trace amount of a strong acidic material, and a fiber product using the same.

BACKGROUND ART

With the recent changes in industrial structure and working environment, the amount of toxic chemicals being used is on the increase. Accordingly, the issues on the manufacture, use, and treatment of waste chemicals have been raised, and human bodies are now exposed to environments where chemicals are present not only in the working sites but also via various routes. Nevertheless, the development of protective clothes which can detect the changes in working environment according to the use of toxic chemicals is far from satisfaction.

As such, attempts were made to prepare protective clothes by applying pH-detecting chromic dyes, however, the conventional pH-detecting chromic dyes had problems in that they could not be dyed into fibers, and that, even they were dyed, the chromic action of colors according to pH change disappeared in the dyed state. Additionally, the chromic dyes had a problem in that they were discolored and faded by laundering, sunlight, etc., thus are not usable.

Therefore, attempts have been made to develop a novel dye for acid detection, and a previous reference (*Acta Crystallographica Section C Crystal structure Communications*, 2009, 65 (10), 543-548) discloses that 4-(phenyldiazenyl)aniline reacts with 5-sulfosalicylic acid or benzenesulfonic acid to form a proton-transfer red-black dye and that 4-(phenyldiazenyl)aniline forms a 1:2 non-transfer complex compound with 3,5-dinitrobenzoic acid. However, these structures only describe the color changes by the binding with a particular acidic compound, and they cannot be considered to have characteristics for pH-detection.

Meanwhile, hydrofluoric acid is an aqueous solution of hydrofluoride (HF) and a colorless pungent liquid, which fumes in the air, is toxic and has small surface tension and strong penetration ability, and thus can strongly penetrate into the skin or the mucus. Therefore it requires special attention for its handling. Hydrofluoric acid has good reactivity, and reacts with oxides of metals such as alkali, alkali earth metal, lead, zinc, silver, etc., hydroxides, or carbonates thereby forming fluorides. In plating, hydrofluoric acid is used in a plating bath for tin, lead, solder, chromium, etc., as a fluoride bath. Additionally, hydrofluoric acid is also used for corrosion of glass, sand removal of the casting, treatment of stainless steel surface, pre-treatment of plating, etc.

Currently, companies which use hydrofluoric acid are equipped with accident prevention system by installing a gas leak alarm device against the leakage of hydrofluoric acid, and additionally, infrared cameras or CCTVs are installed for use. The gas leak alarm device serves to detect a combustible gas or a gas with toxic materials, reveals the concentrations of these gases, and automatically alarms in their preset gas concentrations. However, the gas leak alarm device does not alarm until the gases reach a certain concentration or higher, and thus the gas leak alarm device was not sufficient for immediate response for on-site workers. Furthermore, the gas leak alarm device also becomes a cause for serious accidents due to its malfunction.

In this regard, there is an urgent need for the development of protective clothes which help workers to easily detect acid in work sites and actively recognize dangerous situation thereby preventing the damages from safety accidents and secondary accidents.

For the development of protective clothes which can help workers to actively recognize the harmful situation of strong acid thereby preventing the workers from the damages of safety accidents and secondary accidents, the present inventors have endeavored to develop a dye, which changes its color when exposed to an acidic material and maintains its characteristics even after it is dyed into a fiber. As a result, they have discovered that when a fiber was dyed using the N,N-dialkylaniline azobenzene, the resulting fiber showed a color change to a trace amount of acidic material and also showed high color fastness when dyeing, thereby completing the present invention.

SUMMARY OF THE INVENTION

An object of the present invention is to provide a monoazo-based dye for acid detection, which changes color upon addition of or exposure to acid.

Another object of the present invention is to provide a fiber dyed with a monoazo-based dye for acid detection.

A further object of the present invention is to provide clothes prepared using yarns containing fibers dyed with a monoazo-based dye for acid detection.

To achieve the above objects, the present invention provides a monoazo-based dye for acid detection, which is represented by the following Formula 1 and changes color upon addition of or exposure to acid:

[Formula 1]

In the above Formula 1, n is an integer of 2 to 11.

The compound of Formula 1 of the present invention is a compound, in which the terminal amino group substituent of the N,N-di$C_{3\text{-}12}$ alkylaniline azobenzene structure is a $C_{3\text{-}12}$alkyl, and the compound specifically changes its color upon addition of or exposure to acid and, even after being dyed into a fiber, the compound still retains its high color fastness thus capable of changing the color of the dyed fiber upon addition of or exposure to acid.

Regarding the 'n' in Formula 1, the higher the carbon number the greater the dyeability during the dyeing of a superhydrophobic fiber and also the higher the various color fastness. However, when the carbon number exceeds the above range, there is a difficulty in the dyeing process such as dispersion, whereas when the carbon number is below, the color fastness to laundering, abrasion, and sublimation become extremely poor (almost at the 1$^{st}$ degree to the 2$^{nd}$ degree) and it is impossible to use the dye although the dye can be dyed into a fiber.

In an exemplary embodiment of the present invention, an experiment for measuring the color intensity of a fiber during the dyeing according to the carbon number of the alkyl group of the N,N-dialkylaniline azobenzene was performed. As a result, it was confirmed that the color intensity of the fiber distinctively increased in a $C_3$ alkyl. Additionally, it was confirmed that the color intensity of the fiber gradually decreased from a $C_6$ alkyl and thereafter. Additionally, it was confirmed that the color intensity of the fiber was too low to perform the dyeing work from a $C_{13}$ alkyl and thereafter. Accordingly, it was confirmed that when the length of an alkyl group becomes long, the size of the dye molecule becomes too big to penetrate into a fiber, thus being unable to perform the dyeing process.

Additionally, only the N,N-di$C_{3-12}$alkylaniline azobenzene structure of Formula 1 shows the change in color upon addition of or exposure to acid. For example, when other substituents such as a nitro group or halogen are substituted, the characteristic of the present invention, i.e., color change upon addition of or exposure to acid, cannot be exhibited.

The dye according to the present invention may be synthesized by a general diazotization-coupling reaction. The diazotization can be performed by dissolving an aniline compound as a diazo component into water, which was added with hydrochloric acid, and added with sodium nitrite ($NaNO_3$) after dissolving it in water.

N,N-di-$C_{3-12}$ alkyl-aniline, as a coupler, is dissolved in ethanol and then added into the diazotized solution and reacted to synthesize a compound of Formula 1, and the desired dye is obtained by separation through filtration. The dye of the present invention can be manufactured by a simple process, and thus can be produced in an inexpensive and highly efficient manner from the industrial aspect.

In the present invention, the acid to be added or exposed is in the form of a gas. More specifically, the gas may be in a gas form at room temperature (0° C. to 30° C.) under the pressure of 1 atm. Additionally, the discoloration also occurs in the same manner by an acid in a liquid form, and all functional properties can be expressed and maintained in the same manner in the dye of the present invention and the fibers dyed with the same.

Additionally, the acid is a strong acid in the range of pH 0.1 to pH 5, and preferably, hydrochloric acid, hydrofluoric acid, sulfuric acid, or a mixture thereof, although there is no limitation in the kind of the strong acid. In an exemplary embodiment of the present invention, an experiment was performed using hydrochloric acid, but the same color change can occur using a hydrofluoric acid gas. In the case of sulfuric acid, the acid hardly turns into a gaseous phase due to its high boiling point, and when sulfuric acid is converted into a gaseous phase by heat treatment, the same result regarding color change as in the experimental example can be observed.

In the present invention, the acid to be added or exposed, in a concentration of 3 ppm or higher, can change color in the presence of a trace amount of an acid, without limitation in its upper limit. For example, the amount of the acid may be in the range of 3 ppm to 1000 ppm. According to an exemplary embodiment of the present invention, the acid showed a chromic property even in an extremely diluted concentration exhibiting a color difference before and after color change ($\Delta E$) of 10, and thus anyone with a normal vision could easily recognize the color change.

In the present invention, the dye changes color upon addition of or exposure to acid, and upon removal of the acid, returns to its original color. The original color of the monoazo-based dye of Formula 1 of the present invention shows a yellow color and changes into red upon addition of or exposure to acid. Additionally, when the dye is mixed with other pigments (dyes), various color change can be achieved, and the mixed dye shows bright and clear yellow and red colors which can be used as a trichromatic dye, and thus mixing of colors can be easily performed.

In the present invention, the dye can change its color within 5 seconds to 30 seconds upon addition of or exposure to acid. According to an exemplary embodiment of the present invention, the dye showed a chromic property within 5 seconds upon addition of or exposure to acid, and the dye showed a distinct color change in 30 seconds so that anyone could easily recognize the color change.

Additionally, according to an exemplary embodiment of the present invention, the rate of color return upon removal of acid was rather slow compared to the rate of color change, however, the color was returned to the original yellow by natural ventilation for about 5 minutes (300 seconds). Furthermore, the chromic property of the dye can occur continuously and its ability of color change can be maintained semi-permanently by repeating the exposure to an acid gas and the natural ventilation, regardless of the features of color change.

Additionally, the present invention provides a fiber dyed with a monoazo-based dye for acid detection, represented by the following Formula 1, which changes color upon addition of or exposure to acid.

In the present invention, the fiber may be at least one fiber selected from the group consisting of polyester fiber, nylon fiber, acetate fiber, acrylic fiber, polypropylene fiber, and polyethylene fiber; or a blended fiber thereof.

In the present invention, when the 'n' in Formula 1 is an integer of 2 to 3, the dye can be easily applied to dyeing polyester fiber, nylon fiber, acetate fiber, acrylic fiber, or a blended fiber thereof.

When the 'n' in Formula 1 is an integer of 2 to 3, the dye has weak hydrophobicity, and thus N,N-di$C_{3-4}$alkylaniline azobenzene, due to its high affinity to polyester fiber, nylon fiber, acetate fiber, or acrylic fiber, can be easily dyed to polyester fiber, nylon fiber, acetate fiber, or acrylic fiber, which have weak hydrophobicity.

In the present invention, when the 'n' in Formula 1 is an integer of 4 to 11, the dye can be easily applied to dyeing polypropylene fiber, polyethylene fiber, or a blended fiber thereof.

When the in Formula 1 is an integer of 4 to 11, the dye has strong hydrophobicity, and thus the structure of N,N-di$C_{5-12}$alkylaniline azobenzene has high affinity for polypropylene fiber or polyethylene fiber, which have extreme hydrophobicity, and can be easily dyed.

In the present invention, the dye can show color fastness of the 4$^{th}$ degree to the 5$^{th}$ degree during the dyeing on a fiber. Additionally, in an exemplary embodiment of the present invention, when the dyeing is performed on polypropylene- or polyethylene fiber, washing, abrasion, and light fastness were all shown to be in the range of the 4$^{th}$ degree to the 5$^{th}$ degree, thus confirming the superior durability of the dye.

Additionally, the present invention provides clothes prepared using yarns dyed with a monoazo-based dye for acid detection represented by Formula 1, which changes color upon addition of or exposure to acid.

In the present invention, the clothes may be protective clothes or working clothes.

In the present invention, the yarns of the clothes may be manufactured using polyester fiber, nylon fiber, acetate fiber, acrylic fiber, polypropylene fiber, or polyethylene fiber, which were dyed with a monoazo-based dye for acid detection represented by Formula 1, which changes color upon addition of or exposure to acid, or prepared using a blended fiber containing fibers other than those described above.

Since the monoazo-based dye for acid detection of the present invention can be dyed well to polyester fiber, nylon fiber, acetate fiber, acrylic fiber, polypropylene fiber, or polyethylene fiber, clothes can be manufactured using these fibers or a blended fiber containing these fibers.

In particular, polypropylene fiber is a fiber having strength in the range of 4.5 g/d to 9.0 g/d and elongation of 25% to 60%. Polypropylene fiber not only has a mechanical property similar to that of polyester fiber, which is most commonly used at present, but also has excellent drug resistance. Furthermore, polypropylene fiber has a specific gravity of 0.90 to 0.92, which is the lowest among the fibers, and thus has been known as a fiber material floating in water, and also has been widely known as a material for protective clothes or working clothes used in semiconductor industrial facilities, etc.

However, the polypropylene fiber is known as a non-dyeable fiber because it is almost impossible to perform dyeing with any dye in a dyeing system mediated by water, due to its unique extreme hydrophobicity.

As such, in an exemplary embodiment of the present invention, when the N,N-di$C_{5-12}$alkylaniline azobenzene dye, in which 'n' in Formula 1 is an integer of 4 to 11, was used, the polypropylene fiber could be dyed into yellow, and the polypropylene fiber also showed high color fastness, thus confirming that there was no problem of discoloration or fading due to washing and light-exposure. Additionally, the color changed into red upon addition of or exposure to acid thus exhibiting the acid-detecting property. Furthermore, the dye returned to its original color when the acid was removed thus confirming that the reversibility is semi-permanent.

Accordingly, since the fiber dyed with the dye of the present invention changes color within a few seconds upon exposure to a trace amount of a strong acidic material, when protective or working clothes are manufactured as such, workers can visually recognize the leakage of hydrofluoric acid, sulfuric acid, or hydrochloric acid, etc., in real thus capable of preventing or protecting themselves from accidents.

Advantageous Effects of the Invention

The present invention relates to a monoazo-based dye for acid detection, which changes color within a few seconds upon exposure to a trace amount of a strong acidic material, and returns to the original color when the acid is removed. Additionally, a fiber dyed with the dye of the present invention exhibits high color fastness, and thus is not discolored and faded by laundering or sunlight. In addition, there is an effect of preventing secondary contamination at an accident scene and serious accidents from harmful environmental factors, when protective or working clothes are manufactured applying the effect, thereby providing a function enabling workers to recognize an exposure to acid in real time in the case of an exposure to an acid-contaminated environment.

DETAILED DESCRIPTION OF THE INVENTION

Hereinafter, the present invention will be described in detail with reference to the following Examples. However, the Examples of the present invention may be embodied in many different forms and these Examples should not be construed as limiting the scope of the present invention.

The starting materials and reaction reagents among the compounds used below were the reagents from Aldrich, and all solvents were pure and thus used without drying or purification.

Example 1: Preparation of (E)-N,N-dihexyl-4-(phenyldiazenyl)benzenamine Compound (General Name: N,N-dihexylanilineazobenzene) Dye Aniline (0.01 mole) was added into water (5 mL), added with hydrochloric acid (35%; 2.19 g) and dissolved. Sodium nitrite (0.01 mole) was dissolved in water (5 mL) and slowed added into the dissolved aniline while maintaining the temperature at 0° C. to 5° C. to proceed with a diazotization reaction. The resulting diazotized solution was added with propionic acid (1.5 mL) and acetic acid (8.5 mL).

N,N-dihexylaniline (0.01 mole) as a coupler was dissolved/emulsified in ethanol (40 mL) and the coupler solution was added to the diazotized solution and reacted.

In about 2 hours thereafter, the reaction was completed, added with distilled water (200 mL), and allowed to stand for 24 hours for the phase separation of the synthesized dye. The separated distilled water in the lower layer was removed by release and placed thereat using an excess amount of distilled water, and this whole process was repeated 3 times for purification.

Upon completion of the purification using distilled water, the synthesized dye was obtained by dissolving in benzene, which has high solubility for the dye, and the distilled water contained in part of the benzene was removed, and finally, the benzene was evaporated to obtain the title compound represented by Formula 2 below (yield; 75%).

[Formula 2]

Figure 1:
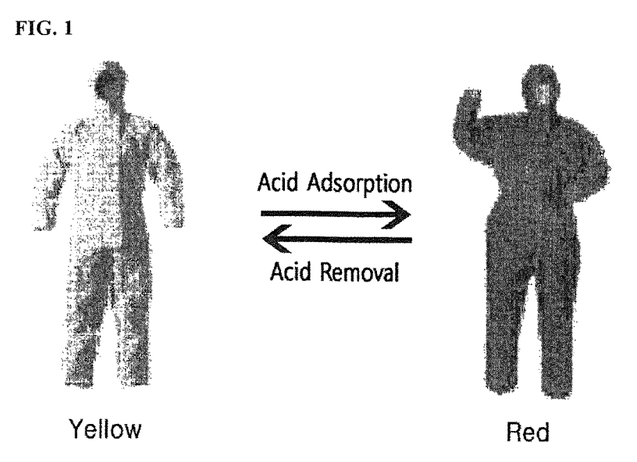
FIG. 1 shows the color change behavior when protective clothes are manufactured dying the dye prepared in Example 1 of the present invention to polypropylene fiber.
Figure 2:
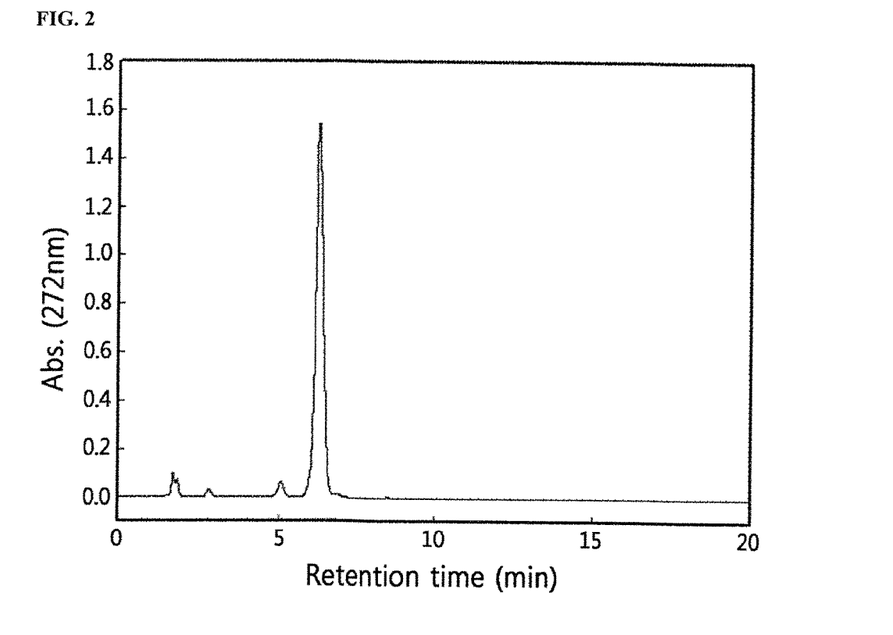
FIG. 2 shows the result of HPLC of the compound prepared in Example 1 of the present invention.
Figure 3:
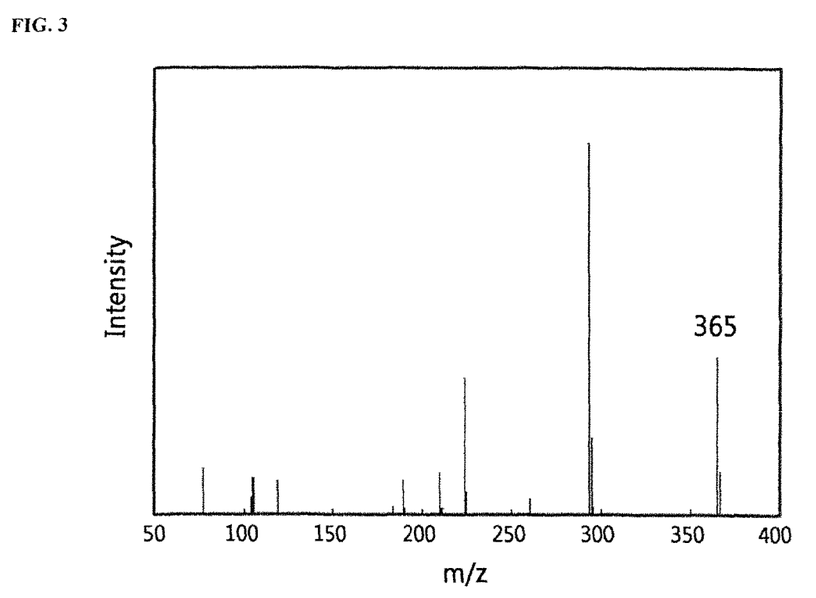
FIG. 3 shows the result of GC-MS of the compound prepared in Example 1 of the present invention.

In order to confirm whether the above compound of the present invention was prepared, HPLC, GC-MS, and NMR analyses were performed. As a result of the HPLC analysis, the peak, which appeared when the retention time was about 6.5 minutes, was the peak for the above title compound, and the purity of the compound after synthesis and purification was about 95% (FIG. 2). Additionally, as a result of the GC-MS analysis, it was confirmed that the predicted molecular weight of the title compound was 365 and also confirmed that the title compound was obtained exactly at 365 as a result of the GC-MS analysis. The peaks which appeared below 365 were confirmed to be peaks occurring due to fragmentation (FIG. 3).

Figure 4:
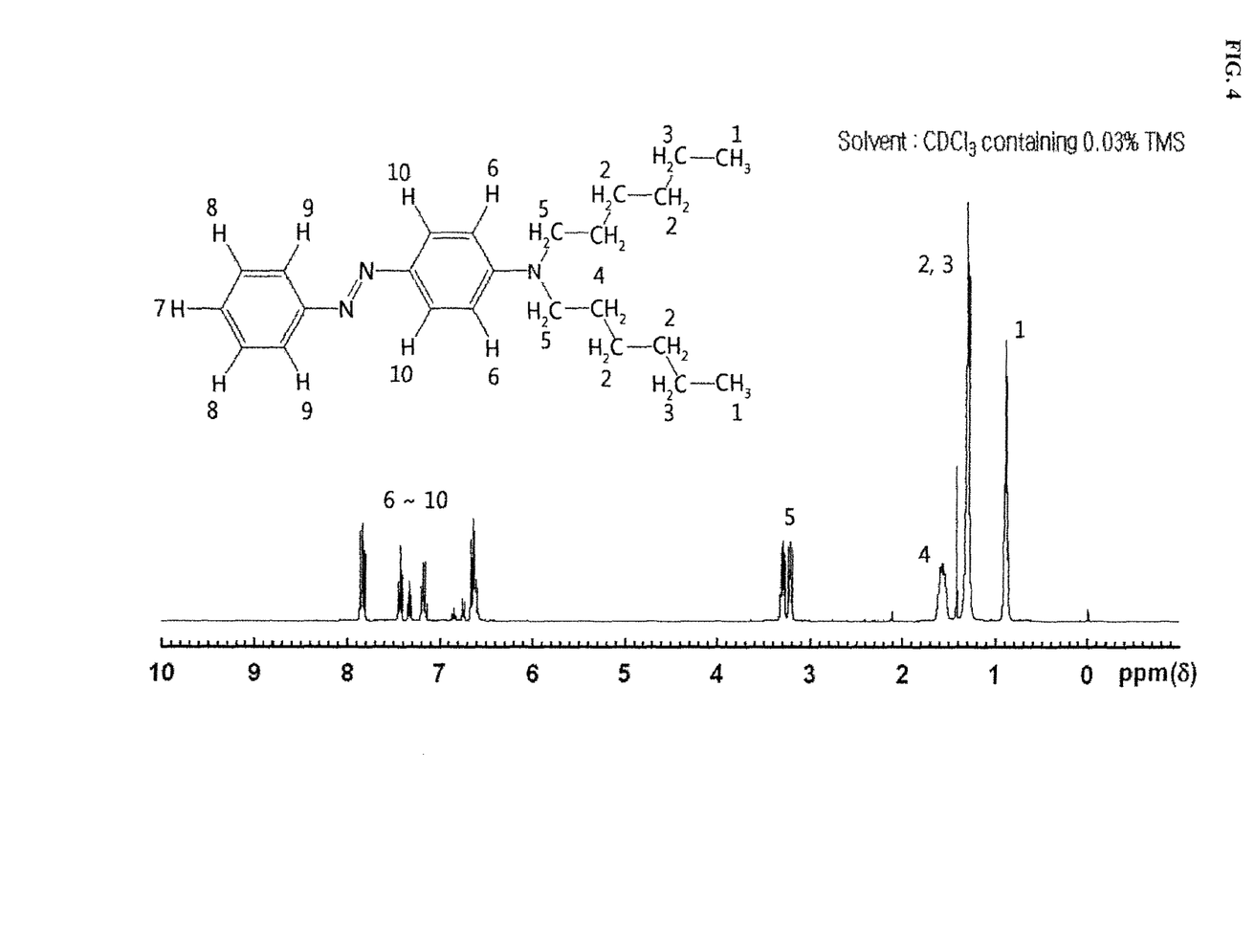
FIG. 4 shows the result of NMR of the compound prepared in Example 1 of the present invention.

Additionally, the synthesis of the title compound was confirmed by observing the appearances of the peaks of 5 kinds of aliphatic hydrogen and the peaks of 5 kinds of aromatic hydrogen as a result of NMR analysis (FIG. 4).

Example 2: Preparation of (E)-N,N-dipropyl-4-(phenyldiazenyl)benzenamine Compound (General Name: N,N-dipropylanilineazobenzene) Dye The dye of the title compound represented by Formula 3 below was obtained in the same manner as described in Example 1, except that N,N-dipropylaniline was used as the coupler.

[Formula 3]

In order to confirm whether the above compound of the present invention was prepared, GC-MS analysis was performed. As a result of the GC-MS analysis, it was confirmed that the predicted molecular weight of the title compound was 281 and also confirmed that the title compound was obtained exactly at 281 as a result of the GC-MS analysis. The peaks which appeared below 281 were confirmed to be peaks occurring due to fragmentation.

Example 3: Preparation of (E)-N,N-dibutyl-4-(phenyldiazenyl)benzenamine Compound (General Name: N,N-dibutylanilineazobenzene) Dye The dye of the title compound represented by Formula 4 below was obtained in the same manner as described in Example 1, except that N,N-dibutylaniline was used as the coupler.

[Formula 4]

In order to confirm whether the above compound of the present invention was prepared, GC-MS analysis was performed. As a result of the GC-MS analysis, it was confirmed that the predicted molecular weight of the title compound was 309 and also confirmed that the title compound was obtained exactly at 309 as a result of the GC-MS analysis. The peaks which appeared below 309 were confirmed to be peaks occurring due to fragmentationdivision.

Example 4: Preparation of (E)-N,N-dipentyl-4-(phenyldiazenyl)benzenamine Compound (General Name: N,N-dipentylanilineazobenzene) Dye The dye of the title compound represented by Formula 5 below was obtained in the same manner as described in Example 1, except that N,N-dipentylaniline was used as the coupler.

[Formula 5]

In order to confirm whether the above compound of the present invention was prepared, GC-MS analysis was performed. As a result of the GC-MS analysis, it was confirmed that the predicted molecular weight of the title compound was 337 and also confirmed that the title compound was obtained exactly at 337 as a result of the GC-MS analysis. The peaks which appeared below 337 were confirmed to be peaks occurring due to fragmentation.

Example 5: Preparation of (E)-N,N-diheptyl-4-(phenyldiazenyl)benzenamine Compound (General Name: N,N-diheptylanilineazobenzene) Dye The dye of the title compound represented by Formula 6 below was obtained in the same manner as described in Example 1, except that N,N-diheptylaniline was used as the coupler.

[Formula 6]

In order to confirm whether the above compound of the present invention was prepared, GC-MS analysis was performed. As a result of the GC-MS analysis, it was confirmed that the predicted molecular weight of the title compound was 393 and also confirmed that the title compound was obtained exactly at 393 as a result of the GC-MS analysis. The peaks which appeared below 393 were confirmed to be peaks occurring due to fragmentationdivision.

Example 6: Preparation of (E)-N,N-dioctyl-4-(phenyldiazenyl)benzenamine Compound (General Name: N,N-dioctylanilineazobenzene) Dye The dye of the title compound represented by Formula 7 below was obtained in the same manner as described in Example 1, except that N,N-dioctylaniline was used as the coupler.

[Formula 7]

In order to confirm whether the above compound of the present invention was prepared, GC-MS analysis was performed. As a result of the GC-MS analysis, it was confirmed that the predicted molecular weight of the title compound was 421 and also confirmed that the title compound was obtained exactly at 421 as a result of the GC-MS analysis. The peaks which appeared below 421 were confirmed to be peaks occurring due to fragmentation.

Example 7: Preparation of (E)-N,N-dinonyl-4-(phenyldiazenyl)benzenamine Compound (General Name: N,N-dinonylanilineazobenzene) Dye The dye of the title compound represented by Formula 8 below was obtained in the same manner as described in Example 1, except that N,N-dinonylaniline was used as the coupler.

[Formula 8]

In order to confirm whether the above compound of the present invention was prepared, GC-MS analysis was performed. As a result of the GC-MS analysis, it was confirmed that the predicted molecular weight of the title compound was 449 and also confirmed that the title compound was obtained exactly at 449 as a result of the GC-MS analysis. The peaks which appeared below 449 were confirmed to be peaks occurring due to fragmentation.

Example 8: Preparation of (E)-N,N-didecyl-4-(phenyldiazenyl)benzenamine Compound (General Name: N,N-didecylanilineazobenzene) Dye The dye of the title compound represented by Formula 9 below was obtained in the same manner as described in Example 1, except that N,N-didecylaniline was used as the coupler.

[Formula 9]

In order to confirm whether the above compound of the present invention was prepared, GC-MS analysis was performed. As a result of the GC-MS analysis, it was confirmed that the predicted molecular weight of the title compound was 477 and also confirmed that the title compound was obtained exactly at 477 as a result of the GC-MS analysis. The peaks which appeared below 477 were confirmed to be peaks occurring due to fragmentation.

Example 9: Preparation of (E)-4-(phenyldiazenyl)-N,N-diundecylbenzenamine Compound (General Name: N,N-diundecylanilineazobenzene) Dye The dye of the title compound represented by Formula 10 below was obtained in the same manner as described in Example 1, except that N,N-diundecylaniline was used as the coupler.

[Formula 10]

In order to confirm whether the above compound of the present invention was prepared, GC-MS analysis was performed. As a result of the GC-MS analysis, it was confirmed that the predicted molecular weight of the title compound was 505 and also confirmed that the title compound was obtained exactly at 505 as a result of the GC-MS analysis. The peaks which appeared below 505 were confirmed to be peaks occurring due to fragmentation.

Example 10: Preparation of (E)-N,N-didodecyl-4-(phenyldiazenyl)benzenamine Compound (General Name: N,N-didodecylanilineazobenzene) Dye The dye of the title compound represented by Formula 11 below was obtained in the same manner as described in Example 1, except that N,N-didodecylaniline was used as the coupler.

[Formula 11]

In order to confirm whether the above compound of the present invention was prepared, GC-MS analysis was performed. As a result of the GC-MS analysis, it was confirmed that the predicted molecular weight of the title compound was 533 and also confirmed that the title compound was obtained exactly at 533 as a result of the GC-MS analysis. The peaks which appeared below 533 were confirmed to be peaks occurring due to fragmentation.

Comparative Example 1: Preparation of (E)-N,N-dimethyl-4-(phenyldiazenyl)benzenamine Compound (General Name: N,N-dimethylanilineazobenzene) Dye The dye of the title compound represented by Formula 12 below was obtained in the same manner as described in Example 1, except that N,N-dimethylaniline was used as the coupler.

[Formula 12]

In order to confirm whether the above compound of the present invention was prepared, GC-MS analysis was performed. As a result of the GC-MS analysis, it was confirmed that the predicted molecular weight of the title compound was 225 and also confirmed that the title compound was obtained exactly at 225 as a result of the GC-MS analysis. The peaks which appeared below 225 were confirmed to be peaks occurring due to fragmentation.

Comparative Example 2: Preparation of (E)-N,N-diethyl-4-(phenyldiazenyl)benzenamine Compound (General Name: N,N-diethylanilineazobenzene) Dye The dye of the title compound represented by Formula 13 below was obtained in the same manner as described in Example 1, except that N,N-diethylaniline was used as the coupler.

[Formula 13]

In order to confirm whether the above compound of the present invention was prepared, GC-MS analysis was performed. As a result of the GC-MS analysis, it was confirmed that the predicted molecular weight of the title compound was 253 and also confirmed that the title compound was obtained exactly at 253 as a result of the GC-MS analysis. The peaks which appeared below 253 were confirmed to be peaks occurring due to fragmentation.

Comparative Example 3: Preparation of (E)-4-(phenyldiazenyl)-N,N-ditridecylbenzenamine Compound (General Name: N,N-ditridecylanilineazobenzene) Dye The dye of the title compound represented by Formula 14 below was obtained in the same manner as described in Example 1, except that N,N-ditridecylaniline was used as the coupler.

[Formula 14]

In order to confirm whether the above compound of the present invention was prepared, GC-MS analysis was performed. As a result of the GC-MS analysis, it was confirmed that the predicted molecular weight of the title compound was 561 and also confirmed that the title compound was obtained exactly at 561 as a result of the GC-MS analysis. The peaks which appeared below 561 were confirmed to be peaks occurring due to fragmentation.

Comparative Example 4: Preparation of (E)-4-(phenyldiazenyl)-N,N-ditetradecylbenzenamine Compound (General Name: N,N-ditetradecylanilineazobenzene) Dye The dye of the title compound represented by Formula 15 below was obtained in the same manner as described in Example 1, except that N,N-ditetradecylaniline was used as the coupler.

[Formula 15]

In order to confirm whether the above compound of the present invention was prepared, GC-MS analysis was performed. As a result of the GC-MS analysis, it was confirmed that the predicted molecular weight of the title compound was 589 and also confirmed that the title compound was obtained exactly at 589 as a result of the GC-MS analysis. The peaks which appeared below 589 were confirmed to be peaks occurring due to fragmentation.

Comparative Example 5: Preparation of (E)-N,N-dipentadecyl-4-(phenyldiazenyl)benzenamine Compound (General Name: N,N-dipentadecylanilineazobenzene) Dye The dye of the title compound represented by Formula 16 below was obtained in the same manner as described in Example 1, except that N,N-dipentadecylaniline was used as the coupler.

[Formula 16]

In order to confirm whether the above compound of the present invention was prepared, GC-MS analysis was performed. As a result of the GC-MS analysis, it was confirmed that the predicted molecular weight of the title compound was 617 and also confirmed that the title compound was obtained exactly at 617 as a result of the GC-MS analysis. The peaks which appeared below 617 were confirmed to be peaks occurring due to fragmentation.

Experimental Example 1: Experiment on Measurement of Color Intensity During Dyeing of a Chromic Dye for Acid Detection Dyeing was performed on polypropylene fiber using the dye prepared in Examples 1 to 10 and Comparative Examples 1 to 5 at a dye concentration of 5% owf at 130° C. for 1 hour.

The color intensity of the fiber dyed with the dye according to the present invention was indicated after measuring the K/S value at 420 nm, which is the maximum absorption wavelength of the fiber, using the datacolor SF 600 plus. Specifically, the surface reflection rate (R) was measured at 420 nm, which is the maximum absorption wavelength of the fiber, and the result was indicated in color intensity K/S using Equation 1 below.

$$K/S = \frac{(1-R)^2}{2R} \quad \text{[Equation 1]}$$

Figure 5:
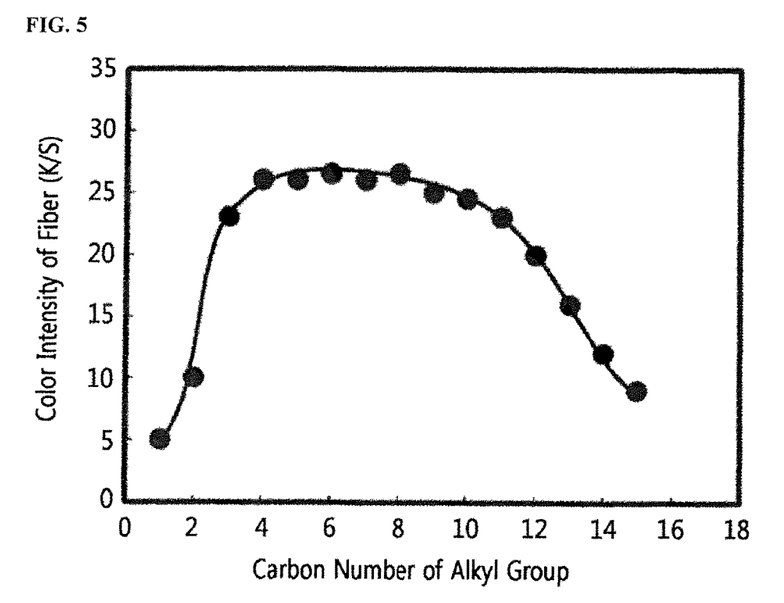
FIG. 5 shows the measurement result of K/S values when the structure of the terminal amino group substituent of the N,N-di$C_{3-12}$ alkylaniline azobenzene, according to Experimental Example 1, is a $C_{1-15}$ alkyl.

The K/S values when terminal amino group substituent of the N,N-dialkylaniline azobenzene structure is a $C_{1-15}$ alkyl were measured and are shown in FIG. 5.

Experimental Example 2: Dyeability of a Chromic Dye for Acid Detection According to Fiber Types Dyeing was performed on polyester fiber, nylon fiber, acetate fiber, acrylic fiber, polypropylene fiber, and polyethylene fiber using the dye prepared in Example 1 at a dye concentration of 5% owf at the dyeing temperature (the dyeing temperature is variably determined according to fiber type and thus follows as described in Table 1 below) for 1 hour.

The fibers dyed with the dyes according to the present invention showed much higher concentrated colors, and in particular, on polypropylene and polyethylene fibers, which are commonly used in anti-chemical clothes, thus indicating extremely concentrated yellow color.

In particular, dyeing was performed on polyester fiber, nylon fiber, acetate fiber, acrylic fiber, polypropylene fiber, and polyethylene fiber using the N,N-dimethylaniline azobenzene (Comparative Example 1) or N,N-diethylaniline azobenzene (Comparative Example 2) dye, prepared in a similar manner to that described in Example 1, using N,N-dimethylaniline (0.01 mole) or N,N-diethylaniline (0.01 mole) as a coupler instead of N,N-dihexylaniline, at a dye concentration of 5% owf at the dyeing temperature (the dyeing temperature is variably determined according to fiber type and thus follows as described in Table 1 below) for 1 hour. As a result, it was confirmed that the polyester fiber, nylon fiber, acetate fiber, and acrylic fiber were dyed, but, due to the extremely poor color fastness to regarding washing, abrasion, and sublimation of the dyes (almost a level of the $1^{st}$ to $2^{nd}$ degree), the yellow color immediately disappeared upon washing, and also the polypropylene fiber and the polyethylene fiber could hardly be dyed.

Experimental Example 3: Chromic Property of a Polypropylene Fiber Dyed with a Chromic Dye for Acid Detection According to an Acid Gas Concentration The concentration of a hydrochloric acid gas was adjusted to 0 ppm to 1000 ppm, and the color change behavior of the polypropylene fibers dyed with the chromic dye in Experimental Example 2 was measured. The results are shown in Table 2 below.

The chromic property was shown in extremely diluted concentrations of the hydrochloric acid gas, and showed a color difference before and after color change (ΔE) of 10. Since anyone with a normal vision could easily recognize the color change in the case of color change (ΔE) of 1, it was confirmed that it is possible to recognize color change in 3 ppm, which is the minimum concentration of the experiment.

Additionally, the color changed from the initial yellow color before the detection of the hydrochloric acid gas to a red color after the detection.

TABLE 1

| Fiber Type | Polyester | Nylon | Acetate | Acryl | Polypropylene | Polyethylene (high strength) |
|---|---|---|---|---|---|---|
| Dyeing Temp. | 130° C. | 100° C. | 100° C. | 100° C. | 130° C. | 130° C. |
| Intensity of Dye Color (Single Wavelength K/S) | 20 | 16 | 19 | 13 | 25 | 24 |
| Visual Color Intensity | Concentrated Color | Moderately Concentrated Color | Concentrated Color | Concentrated Color | Extremely Concentrated Color | Extremely Concentrated Color |

*single wavelength K/S: the color intensity (thickness) of a dyed fiber is indicated in value
*intermediate color: dyeing to a color with an intermediate level of thickness
*moderately concentrated color: dyeing to a color with an intermediate level to a thick color
*concentrated color: dyeing to a thick color
*extremely concentrated color: dyeing to a very thick color

TABLE 2

| Conc. of Acid Gas (ppm) | 0 | 3 | 5 | 10 | 20 | 50 | 100 | 500 | 1000 |
|---|---|---|---|---|---|---|---|---|---|
| Chromic Property (ΔE) | 0 | 10 | 12 | 15 | 17 | 20 | 22 | 25 | 30 |
| Possibility of Naked-Eye Recognition | — | possible | possible | possible | possible | possible | possible | possible | possible |

*chromic property (ΔE): value indicating the difference due to the color change between the initial yellow color before the detection of an acid gas and the red color after the detection of an acid gas Experimental Example 4: Rate of Color Change of a Polypropylene Fiber Dyed with a Chromic Dye for Acid Detection According to the Detection of an Acid Gas (3 ppm)

The time for color change was examined in 3 ppm, which is the minimum experimental concentration of the hydrochloric acid gas. As a result, the chromic property (ΔE) was shown to be 3 or higher within 5 seconds after being exposed to the hydrochloric acid gas, and the color difference was 9 or higher in about 30 seconds after the exposure, and thus normal people could recognize the color change.

TABLE 3

| Time (sec) | 0 | 5 | 10 | 15 | 20 | 30 | 50 | 100 | 200 |
|---|---|---|---|---|---|---|---|---|---|
| Chromic Property (ΔE) | 0 | 3 | 5 | 7 | 8 | 9 | 9 | 10 | 10 |
| Possibility of Naked-Eye Recognition | — | possible | possible | possible | possible | possible | possible | possible | possible |

*chromic property (ΔE): value indicating the difference due to the color change between the initial yellow color before the detection of an acid gas and the red color after the detection of an acid gas Experimental Example 5: Rate of Color Return Upon Removal of an Acid Gas (Natural Ventilation) after Detection of the Acid Gas (3 ppm) by a Polypropylene Fiber Dyed with a Chromic Dye for Acid Detection The dye prepared in Example 1 showed a phenomenon that its original yellow color changed upon detection of a hydrochloric acid gas into a red color, and upon removal of the hydrochloric acid gas (by natural ventilation) returned to its original yellow color. In this regard, the rate of color return was examined and the results are shown in Table 4 below. Although the color return to the original color required slightly more time compared to the rate of color change upon detection of a hydrochloric acid gas, the chromic property to return to the original color (yellow) by natural ventilation for about 5 minutes (300 seconds).

TABLE 4

| Time (sec) | 0 | 30 | 60 | 90 | 120 | 180 | 240 | 300 | 600 |
|---|---|---|---|---|---|---|---|---|---|
| Chromic Property (ΔE) | 10 | 9 | 8 | 7 | 6 | 5 | 3 | 0 | 0 |

Experimental Example 6: Reversible Repetition of Detection of an Acid Gas (3 ppm) by a Polypropylene Fiber Dyed with a Chromic Dye for Acid Detection The dye prepared in Example 1 showed a phenomenon that its original yellow color changed upon detection of a hydrochloric acid gas into a red color, and upon removal of the hydrochloric acid gas (by natural ventilation) returned to its original yellow color. In this regard, for the measurement of reversible repetition of the dye prepared in Example 1, the chromic property (ΔE) was examined by repeating the exposure to a hydrochloric acid and ventilation up to 50 times. As a result, even if repeating the exposure to a hydrochloric acid and ventilation was conducted up to 50 times, it was confirmed that the initial color change behavior was almost not changed as shown in Table 5 below.

TABLE 5

| | No. of Repetition (No.) | | | | | |
|---|---|---|---|---|---|---|
| | 1 | | 5 | | 10 | |
| | Exposure to Gas | Natural Ventilation | Exposure to Gas | Natural Ventilation | Exposure to Gas | Natural Ventilation |
| Chromic Property (ΔE) | 10 | 0 | 10 | 0 | 10 | 0 |

TABLE 5-continued

| | | | No. of Repetition (No.) | | | |
|---|---|---|---|---|---|---|
| | 20 | | 30 | | 50 | |
| | Exposure to Gas | Natural Ventilation | Exposure to Gas | Natural Ventilation | Exposure to Gas | Natural Ventilation |
| Possibility of Naked-Eye Recognition | possible | | possible | | possible | |
| Chromic Property (ΔE) | 10 | 0 | 10 | 0 | 10 | 0 |
| Possibility of Naked-Eye Recognition | possible | | possible | | possible | |

Experimental Example 7: Measurement of Durability (Color Fastness) of a Polypropylene Fiber Dyed with a Chromic Dye for Acid Detection The durability of the dye prepared in Example 1 in response to washing, abrasion, and sunlight described below, on the fiber after dyeing with a polypropylene fiber, was examined. In color fastness, the higher the degree the more excellent the property and the $5^{th}$ degree, which is the possible highest degree, may be obtained. However, in real cases, it is rare to determine the $5^{th}$ degree, and the commercially highest degree of color fastness is indicated as between the $4^{th}$ degree and the $5^{th}$ degree.

The polypropylene fiber dyed with a chromic dye for acid detection of the present invention showed the $4^{th}$ degree to the $5^{th}$ degree of color fastness in all aspects of washing, abrasion, and sunlight, as shown in Table 6, thus confirming its extremely excellent durability.

TABLE 6

| Color Fastness | | | Degree |
|---|---|---|---|
| Washing | Discoloration/Fading | | 4 to 5 |
| | Contamination | Acetate | 4 to 5 |
| | | Cotton | 4 to 5 |
| | | Nylon | 4 to 5 |
| | | Polyester | 4 to 5 |
| | | Acryl | 4 to 5 |
| | | Wool | 4 to 5 |
| Abrasion | Contamination | Dry | 4 to 5 |
| | | Wet | 4 to 5 |
| Sunlight | Discoloration/Fading | | 4 to 5 |

Additionally, the chromic property or dyeing behavior of polypropylene fiber and polyethylene fiber are almost the same, and thus it was confirmed that if the same experiment is performed using the polyethylene fiber dyed with a chromic dye for acid detection of Example 1, instead of the polypropylene fiber dyed with a chromic dye for acid detection of Example 1, the same as/similar to the experimental result described above could be obtained.

As a result of analyzing the color fastness by dyeing using the dye prepared in Example 1, the color fastness of the dye was shown to be excellent both in washing and abrasion having the $4^{th}$ degree or higher, and the color fastness regarding the sublimation was between the $2^{nd}$ degree to the $3^{rd}$ degree. In color fastness to sunlight, the dye showed to be excellent having the $4^{th}$ degree or higher.

When the polypropylene fiber dyed with the dye prepared in Example 1 was exposed to a hydrochloric acid gas, it was visually observed that the initial yellow color of the polypropylene fiber was changed to a red color upon detection, and upon removal of the hydrochloric acid gas, the polypropylene fiber returned to a yellow color.

Based on the above results, it can be confirmed that the application of the finally synthesized dye to protective clothes can help workers to immediately recognize their exposure to an acid gas thereby capable of preventing injuries while working in harmful environments.

The invention claimed is:

1. A method of detecting acid upon exposure to acid gas, comprising detecting a color change on a fiber dyed with a monoazo-based dye of the following Formula 1, when exposed to acid gas having an acid concentration of 3 ppm or above:

[Formula 1]

wherein n is an integer of 2 to 11.

2. The method of claim 1, wherein the acid is a strong acid in the range of pH 0.1 to pH 5.

3. The method of claim 1, wherein the acid is hydrochloric acid, hydrofluoric acid, sulfuric acid, or a mixture thereof.

4. The method of claim 1, wherein the dye changes its color upon exposure to acid gas and returns to its original color when the acid gas is removed.

5. The method of claim 1, wherein the dye changes its color within 5 seconds to 30 seconds upon exposure to the acid gas.

6. The method of claim 1, wherein the fiber is at least one fiber selected from the group consisting of polyester fiber, nylon fiber, acetate fiber, acrylic fiber, polypropylene fiber, and polyethylene fiber, or a blended fiber thereof.

7. The method of claim 1, wherein the fiber is comprised in a yarn.

* * * * *